United States Patent [19]

Davis et al.

[11] Patent Number: 5,236,356
[45] Date of Patent: Aug. 17, 1993

[54] DENTAL SYRINGE TIP AND ADAPTOR

[76] Inventors: Warren Davis, 3026 Sullivan Ave., Rosemead, Calif. 91770; David Wasserman, 2095 Mohigan Way, Las Vegas, Nev. 89109

[21] Appl. No.: 687,039

[22] Filed: Apr. 16, 1991

Related U.S. Application Data

[63] Continuation of Ser. No. 241,081, Sep. 6, 1988, abandoned.

[51] Int. Cl.⁵ .............................................. A61G 17/02
[52] U.S. Cl. ....................................................... 433/80
[58] Field of Search ................................... 433/80, 126

[56] References Cited

U.S. PATENT DOCUMENTS

| | | | |
|---|---|---|---|
| 1,858,056 | 5/1932 | Pieper | 604/150 |
| 3,698,088 | 10/1972 | Austin, Jr. | 433/80 |
| 3,874,083 | 4/1975 | Buckley | 433/80 |
| 4,026,025 | 5/1977 | Hunt | 433/80 |
| 4,248,589 | 2/1981 | Lewis | 433/80 |

Primary Examiner—Gene Mancene
Assistant Examiner—Cindy A. Cherichetti
Attorney, Agent, or Firm—John E. Roethel

[57] ABSTRACT

A clear rigid plastic syringe tip having a central water passageway and three arcuate section air passageways disposed circumferentially about the water passageway. A novel adaptor is used to mount the syringe tip to the handpiece body.

6 Claims, 3 Drawing Sheets

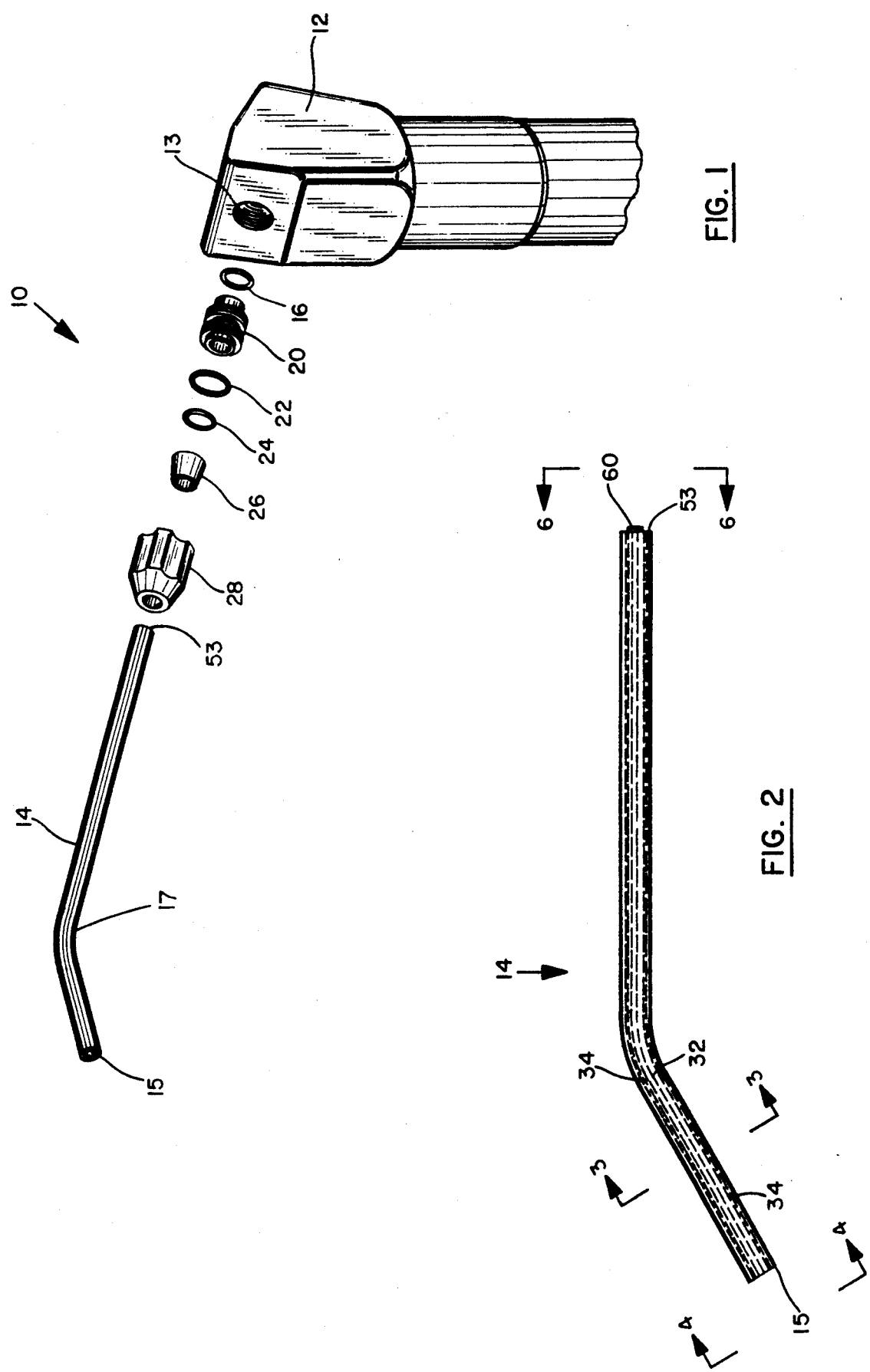

DENTAL SYRINGE TIP AND ADAPTOR

This is a continuation of application Ser. No. 07/241,081, filed Sep. 6, 1988 now abandoned.

BACKGROUND OF THE INVENTION

This invention relates to dental syringe tip assemblies, and more particularly to dental syringe tip assemblies having a disposable tip and an innovative adaptor.

For the past twenty-five years, dentists have been using a three-way syringe. An air tube and a water tube join together at the handpiece. Two operating buttons are provided on the handpiece body to allow activation by the dentist of the air or water. By depressing the air button, air flows out of the tip into the appropriate area of the patient's mouth to dry the field of operation. By depressing the water button, a passive flow of water is emitted to clean and float away debris and congestion from the field of operation. By depressing both buttons simultaneously, a spray of air and water is emitted which flushes away debris which can then be vacuumed from the oral cavity. Typical of a three-way syringe assembly is that shown in U.S. Pat. No. 3,874,083 to Buckley.

During these twenty-five years, there has only been one significant improvement made to this essential piece of dental equipment. In approximately 1979, the tip of the syringe was made removable to allow for sterilization. Before 1979, tips were disinfected and cleaned by simply wiping them with alcohol. With the development of the removable tip, sterilization of each tip could be accomplished through the use of steam or chemical heat procedures. However, if done with the appropriate frequency, the tip becomes clogged and unusable in several months. This is due to minerals and other impurities in the steam used in an autoclave which causes alkaline and calcium deposits to build up in the orifices of the tip which interrupt the flow of air and water from the tip. The air and water orifices in the tip are quite small, so that any irregularities occurring during fabrication will also decrease the life expectancy of the tip. Any plugged of the tip orifices results in both a loss of spray pressure as well as a loss of spray accuracy. Tips are conventionally made out of metal and it would be cost prohibitive to discard a metal tip after only a single use.

With the rising incidence of communicable diseases such as hepatitis and acquire immune deficiency syndrome, extreme care must be taken to prevent the transmission of germs (viral or bacteria) from one patient to the next. With the conventional metal tips, it is necessary to sterilize the tip after each patient use. This is due to a condition that occurs in the end of the tip during use known as water retraction (also called suck-back or draw-back), which is a negative pressure applied to the water line. In a syringe, water retractive is used to prevent siphoning or dripping from the water line. When water retraction occurs, water, saliva and blood form the patient's mouth can be drawn back into the end of the tip and then passed on to the next patient. This provides the opportunity for the transfer of infection from one patient to the next. Also, latent bacterial growth can be promoted in both the tip and the entire water system lines because of the existence of this potentially contaminating material. Both the Center for Disease Control and the American Dental Association recommend that water lines be non-retracting. To further mitigate this possibility of cross-contamination from one patient to the next, the routine sterilization of handpieces as well as air/water syringes is desirable. In the case of handpieces and air/water syringes that cannot be sterilized, it is recommended that other complete cleaning and is infection procedures be followed.

A disposable syringe tip is disclosed in U.S. Pat. No. 4,026,025 to Roderick S. Hunt. The plastic tip is disclosed as flexible and can be easily bent by hand without any special tools or heating. Such a flexible tip would suffer form the limitation that it would not function as a retractor. It is necessary when applying air, water or a spray to the patient's mouth to be able to use the syringe tip as a retractor to move the patient's tongue, cheeks or lips. If the syringe tip were flexible, it would fail to perform this important retraction function.

The syringe tip and mounting collet disclosed in the Hunt patent also have further design limitations. The chamfered surface on the end of the syringe tip effectively directs the air away from the water thereby impeding the formation of the water spray which is so important in a three-way syringe. The small circular air passages further limit the amount of air exiting the end of the tip and these air passages would be subject to being crimped closed when the flexible tip is bent. The syringe tip is press fit on the end of a small nipple on the collet in such a manner that the air and water pressure leaving the handpiece body and entering the syringe tip would lead to a loosening of the press fit thereby causing the syringe tip to dislodge from the nipple. This design is also not adaptable to most three-way piece syringe assemblies on the market.

It is an object of the present invention to alleviate the transmission of germs (viral or bacteria) which cause infection or disease, from one patient to the next, and to eliminate the need to resterilize a syringe tip after each use.

It is a feature of the present invention to provide a clear, plastic disposable rigid syringe tip that is discarded after its use on a single patient, as well as to provide a novel adaptor to connect the disposable syringe tip to the handpiece body.

It is an advantage of the present invention that a more sterile dental environment will be created as well as the flow of air, water or spray form the syringe to the oral cavity will be improved.

Other objects, features and advantages will become apparent when the detailed description and drawings of the present invention are considered.

BRIEF DESCRIPTION OF THE DRAWINGS

FIG. 1 shows an exploded view of a dental syringe assembly incorporating the present invention.

FIG. 2 shows a disposable syringe tip of the present invention.

DETAILED DESCRIPTION OF THE PREFERRED EMBODIMENTS

Figure 3:
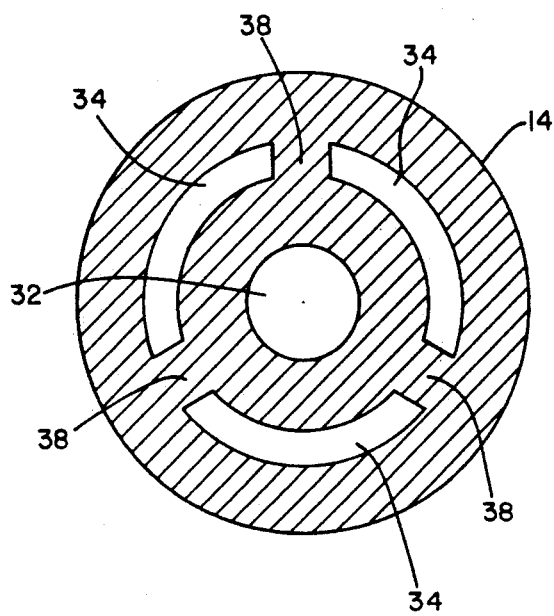
FIG. 3 shows a cross-section taken along line 3—3 of FIG. 2 of the disposable syringe tip of the present invention.

A dental syringe assembly 10 includes a conventional handpiece body 12 on which is mounted a syringe tip 14. The tip 14 is an elongated cylindrical member preferably made of a rigid plastic material. The tip 14 is provided with a bend 17, at preferably an angle of approximately 30°, to provide easy access to any portion of the patient's mouth during use of the syringe assembly. An adaptor 20 screws into a threaded opening 13 in the handpiece body 12 and is sealed toward one end of the adaptor by a first rubber O-ring 16. A second rubber O-ring 22 provides a seal at the midpoint of the adaptor 20.

The tip 14 is press fit into a tapered male connector 21 (see FIGS. 7 and 8) that is mounted axially in the interior of the adaptor 20. A collet 26 and a third O-ring 24 provide a seal for the tip 14 - male connector 21 assembly. A nut 28 comprises a locking assembly and screws onto the threads 44 on the outer surface of adaptor 20 to secure the tip 14, collet 26 and third O-ring 24 in place. Each of the these parts, other than the specific tip 14 and the specific adaptor 20, are the conventional assembly for a three-way syringe tip assembly such as Model No. 23-0090-00 or Model No. 90-0125-00 sold by the Adec Corporation of Newberg, Oregon or the DCI 3-way syringe sold by Air-Con Inc. of Portland, Oregon.

The tip 14 is shown in detail in FIGS. 2 through 6. The tip 14 is designed to be disposable after a single use. The tip material si fabricated in a single-step extrusion process, and is made from any rigid transparent plastic. A rigid plastic is preferred to fulfill the need to use the tip for continued retraction of the cheek, and tongue by the dental operator. In a preferred embodiment, the tip 14 is made form a polycarbonate plastic or other rigid plastic materials. Suitable rigid plastic transparent material is that sold by General Electric Co. under the trademark Ultem 1000 or that sold by Victrex Corp. under the trademark Peek.

As shown in FIGS. 2 through 6, a central water passageway 32 runs the entire length of the tip 14 and is used to deliver water from the handpiece body 12 to the patient's mouth. Three air passageways 34 also run the entire length of the tip 14, are disposed circumferentially about the central passageway 32 and are used to deliver air from the handpiece body 12 to the patient's mouth. If both air and water are delivered through the tip 14 simultaneously, a spray results at the exit end 15 of the tip 14.

In a preferred embodiment, the elongated cylindrical member comprising tip 14 has a diameter in a range generally of 0.140"–0.150", and most preferably has a diameter of approximately 0.145". The water passageway 32 has a diameter in a range of generally 0.035"–0.039", and most preferably has a diameter of approximately 0.036". Each air passageway 34 comprises in cross-section an arcuate section (see FIG. 3) approximately one-third of the circumference of the tip 14. Each arcuate section has a width in a range of generally 0.016"–0.020", and preferably has a width of approximately 0.017". The arcuate sections are separated from one another by thin support segments 38, each having a thickness of approximately 0.018".

While the air passages 34 shown in FIG. 3 are shown in cross-section as an arcuate section, other cross-sectional shapes can also be sued such as rectangular sections, triangular sections and elliptical sections. Likewise, the central water passageway 32, shown in FIG. 3 as having a circular cross-section, can alternatively have other cross-sections such as square, rectangular, elliptical or triangular.

The support segments 38 are also shown in FIG. 3 as being symmetrically oriented about the circumference of the tip 14 approximately 120°±4° apart. It is also possible to asymmetrically orient the support segments 38 about the circumference of the tip which would result in some of the air passages 34 being longer in cross-section than others. Also, while three support segments 38 are shown, as few as two or as many as four or more support segments can also be used.

Figure 4:
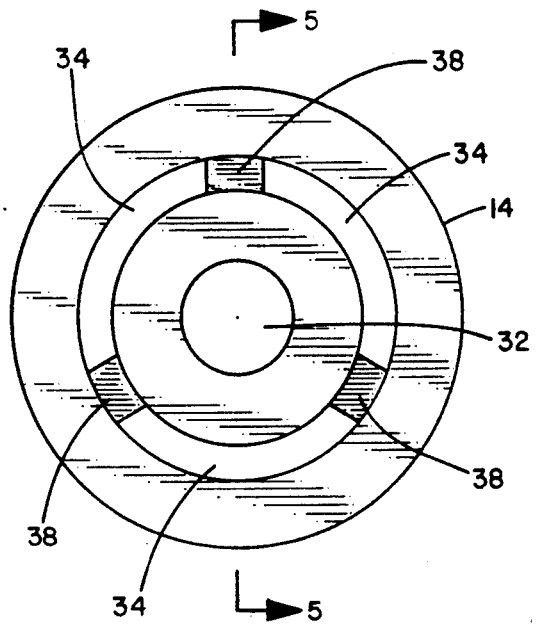
FIG. 4 shows an end view taken along line 4—4 of FIG. 2 of the exit end of the disposable syringe tip of the present invention.
Figure 5:
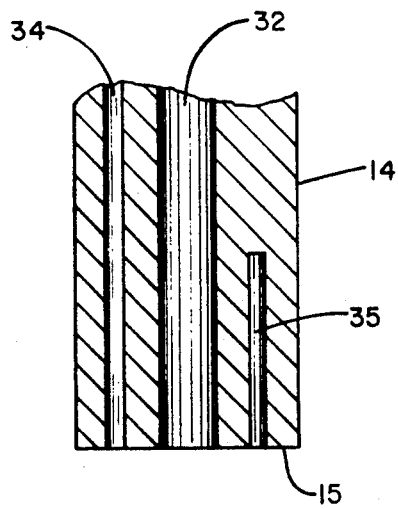
FIG. 5 shows a cross-section of the exit end of the disposable syringe tip taken along line 5—5 of FIG. 4.
Figure 6:
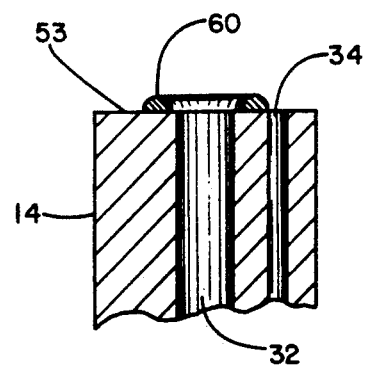
FIG. 6 shows a cross-section of the entrance end of the disposable syringe tip taken along lines 6—6.

As shown in FIGS. 4 and 5, at the exit end 15 of the tip 14, the air passages 34 combine to form a continuous 360° annulus 35 around the water passage 32. This can e achieved during the fabrication of the tip 14 by die-cutting to the desired depth each support segment 38 inward from the exit end 15 of the tip 14. While die-cutting is the preferred way of forming the continuous annulus 35, other methods can be sued to remove the support segments 38 to the desired depth. In the preferred embodiment, the depth of the continuous annulus 35 from the exit end 15 of the tip 14 inward is approximately 0.125".

The continuous annulus 35 achieves a quite effective mixing of the air and water which results in a uniform spray which is easily directed by the dental operator at the needed locations in the patient's mouth.

Figure 7:
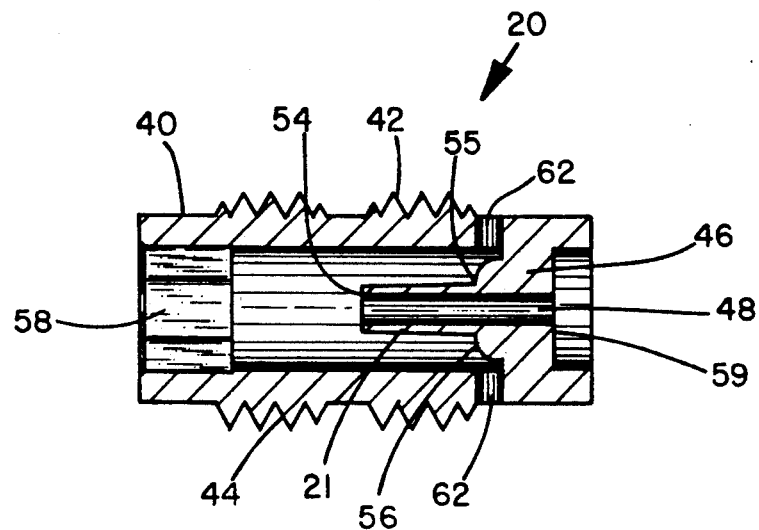
FIG. 7 shows in section the adapter of the present invention.
Figure 8:
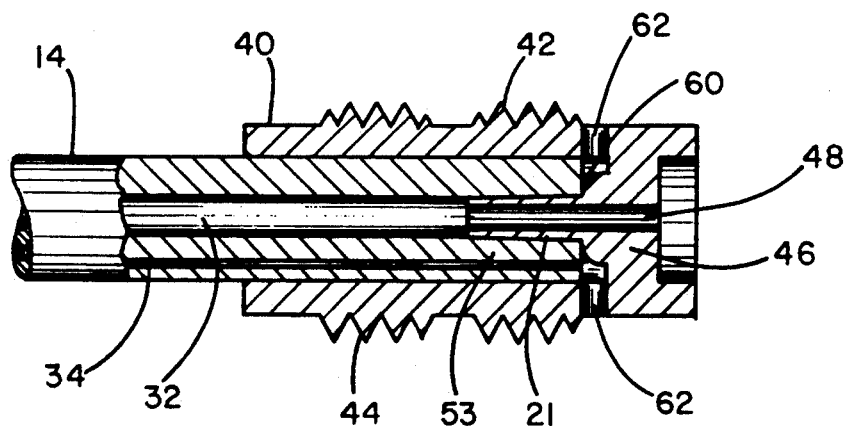
FIG. 8 shows the adaptor with a portion of the syringe tip mounted thereon.

FIGS. 7 and 8 show the adaptor 20 that is used to connect the tip 14 to the handpiece body 12. The adaptor 20, preferably made of metal, comprises a generally cylindrical body having a hollow interior. The exterior wall 40 of the adaptor 20 has a first set of threads 42 for attaching the adaptor 20 to the threaded opening 13 in the handpiece body 12. A baffle 46 extends across the hollow interior of the cylindrical adaptor 20. Formed integrally with the baffle 46 is a male connector 21 formed as a cylindrical member and having an axial opening 48 therethrough. The male connector 21 is tapered to receive the entrance end 53 of the tip 14. The male connector 21 is also formed of metal and has an outer diameter at its forward end 54 of approximately 0.032" and tapers out at its bottom end 55 to a diameter of approximately 0.038". The male connector 21 is press fit into the water passageway 32 of the end 53 of the tip 14. A rounded shoulder 56, which surrounds the bottom of the male connector 21 at the location where the male connector 21 joins the baffle 46, cooperates with a resilient O-ring coating 60 on the entrance end 53 of the tip 14 (see FIG. 6) to form a seal to prevent water form leaking. The baffle 46 communicates at 59 through axial opening 48 with a water line by way of a valve (not shown) in the handpiece body 12.

A plurality of circumferentially arranged channels 62 in the cylindrical body provide openings to allow the air from the handpiece body 12 to pass to the hollow interior of the adaptor 20 and then into the air passageways 34.

A second set of threads 44 is provided on the exterior wall 40 of the adaptor 20. These threads 44 cooperate with the threads in nut 28 to seal the tip 14 to the adaptor 20.

The forward interior portion of the adaptor 20 is provided with an hexagonal cross-section 58 which allows the use of an allen wrench to screw the adaptor 20 into the opening 13 in the handpiece body 12.

The present invention yields significant advantages over the syringe tip-adaptor assemblies used previously. By using a disposable syringe tip, a source of infection and cross-contamination of micro-organisms form one patient to the next is eliminated. When a three-way syringe is used, back pressure is created at the end 15 of the syringe tip 14 whenever the air and water flow is abruptly cut off. This back pressure can cause contaminated water, saliva or blood to be drawn back into the tip openings. If the tip 14 were to be used on a second patient, any micro-organisms in the contaminated water, saliva or blood from the first patient could infect the second patient. A disposable tip 14 used for each patient eliminates this problem.

Existing metal tips should be sterilized prior to use using an autoclave sterilization system. The disposable tip eliminates the need for this autoclave sterilization equipment. Each tip 14 is sanitary during the manufacturing process and is then packaged. A dentist selects a packaged tip, removes the tip rom its package or visually inspects the tip if it is already installed. The clear rigid plastic material from which the tip is made allows visual verification of the tip's sanitary state. If sterilization is required, such can be achieved during the manufacturing process by using any suitable sterilization process, such as gamma ray sterilization.

The prior art metal tip comprised two concentric tubes—an inner water tube surrounded by an outer air tube. In practice, the orifice at the end of the prior art metal tip can be quite irregular causing uneven spray when the air and water flows are effected simultaneously. Uneven flows results in an unpredictable spray pattern.

The extruded tip 14 of the present invention yields very uniform orifices for both air and water at the end 15 of the tip 14. This results in a uniform distribution of air, water or spray. A continuous, uninterrupted air supply through parallel air passageways 34 mitigates air turbulence and therefore produces a more accurate and controlled spray.

The adaptor 20 is different from the prior art adaptors. The tapered male connector 21 with the axial opening 48 provides a mounting location for the tip 14 and keeps the water supply separate from the air supply until they are mixed together at the end 15 of the tip 14 to form the spray. When the air and water are activated simultaneously by the dental operator, the continuous 360° air annulus 35 around the central water passage 32 combines to produce a fine spray.

Other advantages inure from the use of plastic as the material from which the tip 14 is fabricated. A plastic tip will transmit less heat and cold to sensitive tissues in the oral cavity. Plastic tips are not electrically conductive and will not transmit a spark which can occur during modern dental treatments using electro-surgical devices. Also plastic tips are not harmed by the presence of ultrasonic devices.

The tip 14 is fabricated form a good quality, rigid plastic. The bend 17 in the tip 14 is provided during a heat forming step and once the plastic has cooled, the bend is a permanent part of the rigid tip 14. The entire tip fabrication process including extruding the plastic with the central water passage 32 and the arcuate section air passages 34, cutting the plastic extrusion to length, heat forming the bend 17, die-cutting the continuous 360° air annulus 35 and forming the resilient O-ring seal 60 is performed in a special multiple operation machine.

While the invention has been illustrated with respect to several specific embodiments thereof, these embodiments should be considered as illustrative rather than limiting. Various modifications and additions may be made and will be apparent to those skilled in the art. Accordingly, the invention should not be limited by the foregoing description, but rather should be defined only by the following claims.

We claim:

1. A syringe tip adaptor for connecting a syringe tip to a handpiece body comprising;
   a) a generally cylindrical body having a hollow interior,
   b) first screw threads on the exterior surface of the cylindrical body for connecting the cylindrical body to the handpiece body,
   c) channel means for providing an air passage from the handpiece body through the cylindrical body and into an air passageway in the syringe tip, the channel means being disposed relative to the hollow interior of the cylindrical body,
   d) a baffle mounted within the hollow interior of the cylindrical body, the baffle including an axial opening, and
   e) an elongated tapered male connector formed integrally with the baffle and having an axial opening therethrough adapted to cooperate with a central passageway in a syringe tip to provide a water passageway from the handpiece through the adaptor and into the syringe tip whereby when a syringe tip is mounted on the tapered male connector, the syringe tip will be tightly held on the tapered male connector to prevent axial rotation of the syringe tip and to ensure that the air and water passageways do not leak into each other.

2. The adaptor of claim 1 further including a rounded shoulder surrounding the tapered male connector at the location where the male connector joins the baffle to provide a sealing surface when the syringe tip is mounted on the male connector and to provide access for air to enter into air passageways in the syringe tip while at the same time preventing water from leaking out of a water passageway in the syringe tip.

3. The adaptor of claim 1 wherein the channel means comprises a plurality of channels disposed circumferentially around the cylindrical body.

4. The adaptor of claim 1 further comprising second screw threads on the exterior surface of the cylindrical body for connecting the cylindrical body to a locking assembly.

5. The adaptor of claim 1 wherein a forward interior portion of the cylindrical body is provided with an hexagonal cross-section for using an allen wrench to connect the adaptor to the handpiece.

6. A dental syringe assembly comprising a handpiece body including means for mounting a syringe tip assembly to the handpiece body, said syringe tip assembly comprising
   a) a syringe tip adaptor for connecting a syringe tip to a handpiece body comprising
      1) a generally cylindrical body having a hollow interior, 2) first screw threads on the exterior surface of the cylindrical body for connecting the cylindrical body to the handpiece body,
3) channel mans for providing an air passage from the handpiece body through the cylindrical body and into an air passageway in the syringe tip, the channel means being disposed relative to the hollow interior of the cylindrical body,
4) a baffle mounted within the hollow interior of the cylindrical body, the baffle including an axial opening, and
5) an elongated tapered male connector formed integrally with the baffle and having an axial opening therethrough adapted to cooperate with a central passageway in a syringe tip to provide a water passageway from the handpiece through the adaptor and into the syringe tip whereby when a syringe tip is mounted on the tapered male connector, the syringe tip will be tightly held on the tapered male connector to prevent axial rotation of the syringe tip and to ensure that the air and water passageways do not leak into each other, and
b) a syringe tip mounted on the syringe tip adaptor.

* * * * *